United States Patent
Totokawa et al.

(10) Patent No.: US 7,070,829 B2
(45) Date of Patent: Jul. 4, 2006

(54) PRODUCTION METHOD OF GAS SENSOR

(75) Inventors: Masashi Totokawa, Nagoya (JP); Yorishige Matsuba, Tsukuba (JP); Yoshihisa Misawa, Tsukuba (JP); Hideyuki Gotoh, Tsukuba (JP); Katsuhisa Osako, Tsukuba (JP); Masaaki Oda, Chiba (JP); Norimichi Saito, Chiba (JP); Toshihiro Suzuki, Chiba (JP); Noriyuki Abe, Chiba (JP)

(73) Assignees: DENSO Corporation, Kariya (JP); Harima Chemicals, Inc., Hyogo (JP); Ulvac, Inc., Kanagawa (JP)

( * ) Notice: Subject to any disclaimer, the term of this patent is extended or adjusted under 35 U.S.C. 154(b) by 111 days.

(21) Appl. No.: 10/386,831

(22) Filed: Mar. 12, 2003

(65) Prior Publication Data

US 2003/0180446 A1 Sep. 25, 2003

(30) Foreign Application Priority Data

Mar. 15, 2002 (JP) .............................. 2002-072343

(51) Int. Cl.
*B05D 5/12* (2006.01)
*B05D 3/02* (2006.01)

(52) U.S. Cl. ................ 427/115; 427/376.2; 427/383.1; 427/189

(58) Field of Classification Search ................ 427/115, 427/376.2, 383.1, 189; 204/424, 431, 434
See application file for complete search history.

(56) References Cited

U.S. PATENT DOCUMENTS

| 4,397,888 A | * | 8/1983 | Yannopoulos et al. ......... 438/49 |
| 4,592,967 A | * | 6/1986 | Komatsu et al. ............ 428/697 |
| 5,427,740 A | * | 6/1995 | Coles et al. ................... 422/83 |
| 5,629,474 A | * | 5/1997 | Williams .................... 73/23.2 |
| 5,935,275 A | | 8/1999 | Burgard et al. |
| 6,134,946 A | * | 10/2000 | Liu et al. ................... 73/31.06 |

FOREIGN PATENT DOCUMENTS

| JP | 07-318524 | | 8/1995 |
| JP | 08-145933 | * | 6/1996 |
| JP | 11-337517 | | 10/1999 |

OTHER PUBLICATIONS

Search Report dated Jan. 26, 2004 from European Application No. Ep 03 00 5405.

(Continued)

*Primary Examiner*—Brian K. Talbot
(74) *Attorney, Agent, or Firm*—Harness, Dickey & Pierce, PLC

(57) ABSTRACT

To provide a method for producing a sensing film for gas sensors by sintering particles comprising a metal or a metal oxide on a substrate, where the sensing film for gas sensors having excellent sensor properties such as sensitivity and responsibility can be easily and simply formed. A nanometer order particle (100), a dispersant (110) for preventing aggregation of the particles (100), and a scavenger (120) for trapping the dispersant (110) at the sintering are mixed in a solvent (130) to prepare a paste body (140), and this paste body (140) is coated on a base material and fired, thereby forming a sensing film.

14 Claims, 4 Drawing Sheets

U.S. PATENT DOCUMENTS 6,139,816 A      10/2000   Liu et al.
6,395,053 B1 *    5/2002   Fau et al. .................... 75/362
6,537,498 B1 *    3/2003   Lewis et al. ............. 422/82.01

OTHER PUBLICATIONS

Kawi, S. et al, "High-surface-area $SnO_2$: A novel semiconductor-oxide gas sensor", Materials Letters, North Holland Publishing Company, Amsterdam, NL, vol. 34, No. 1-2, Feb. 1998, p. 99-102.

Mulvaney, Paul et al, "Electron transfer in aqueous colloidal $SnO_2$ solutions", Langmuir: Langmuir Mar. 1990, vol. 6, No. 2, Mar. 1990, p. 567-572.

Lu, F. et al., "Nanosized tin oxide as the novel material with simultaneous detection towards CO, H2 and CH4", Sensors and Actuators B, Elsevier Sequoia S.A., vol. 66, No. 1-3, Jul. 25, 2000, p. 225-227.

* cited by examiner

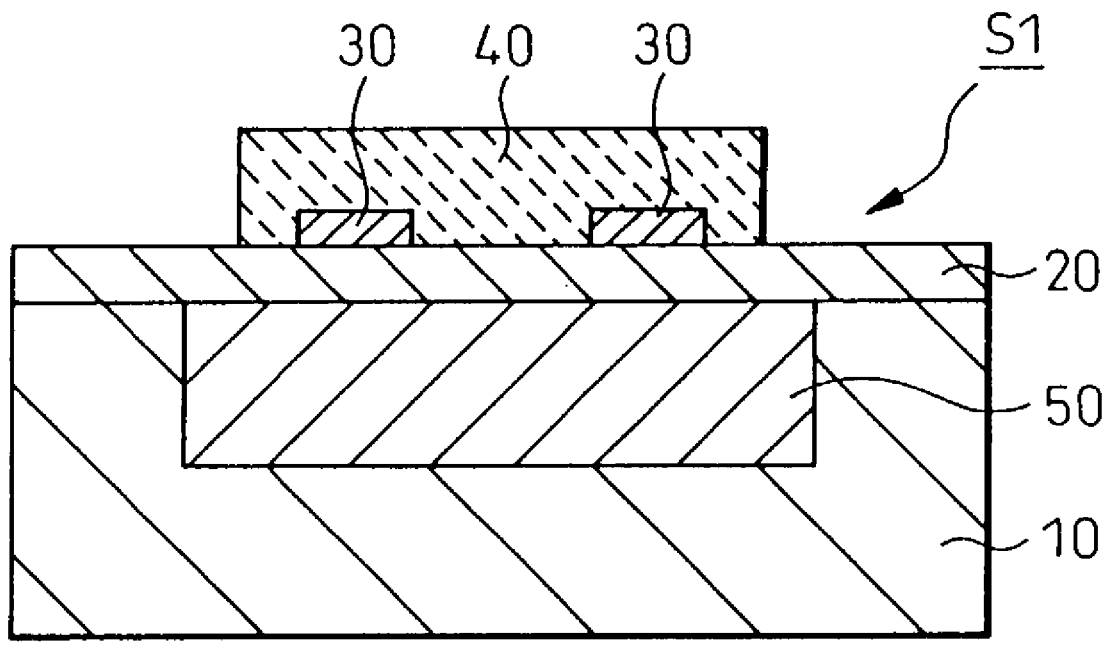

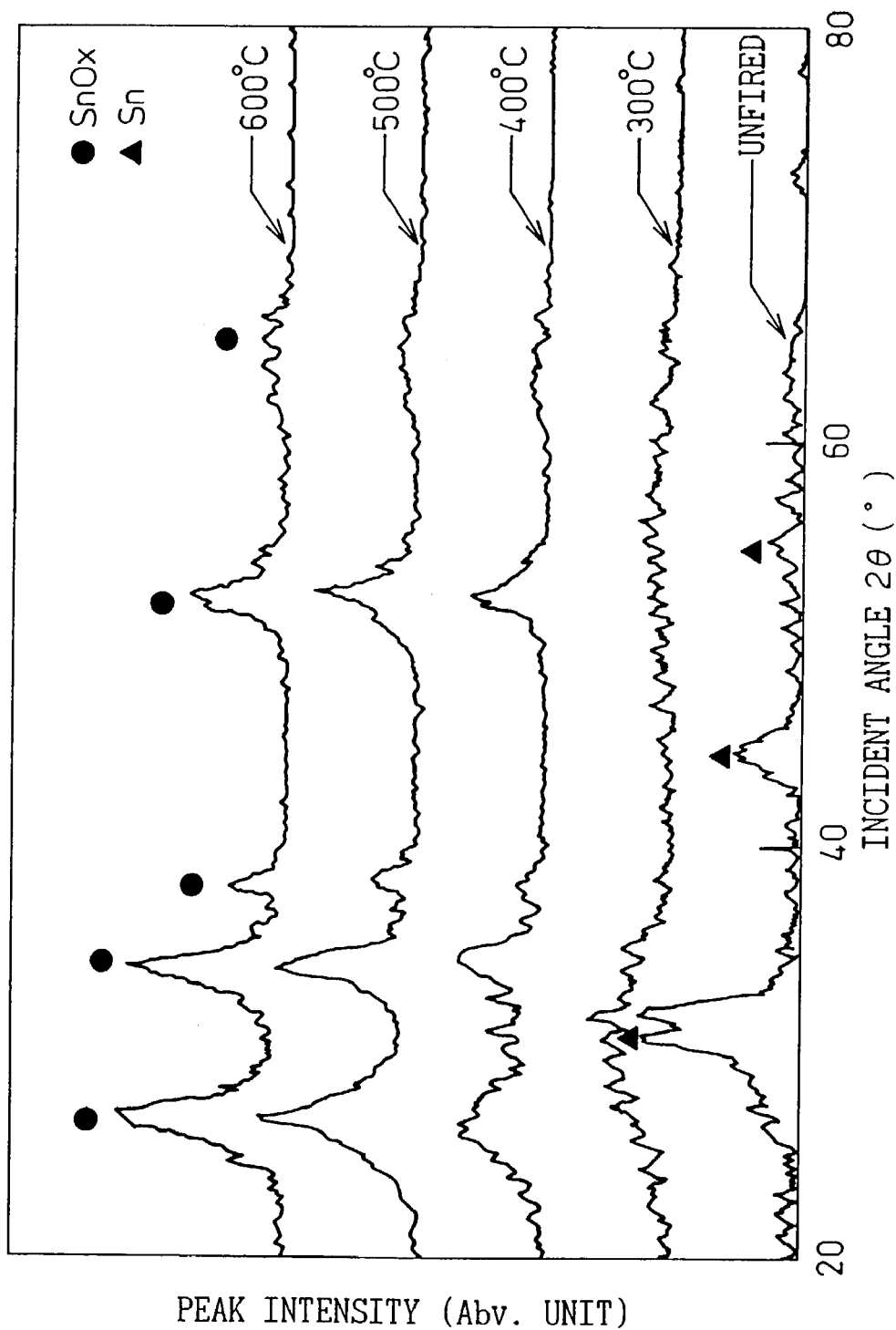

PRODUCTION METHOD OF GAS SENSOR

FIELD OF THE INVENTION

The present invention relates to a method of producing a sensing film for gas sensors by sintering particles comprising a metal or a metal oxide.

DESCRIPTION OF RELATED ART

The sensing film used in gas sensors for detecting a gas such as CO, $NO_x$ and alcohols is conventionally produced by sintering particles comprising a metal or a metal oxide to form a semiconducting oxide film on a substrate. In such a sensing film, a gas to be detected reacts with the film surface and the resistance value of the sensing film changes, whereby the gas can be detected.

The method for forming the semiconducting oxide film is roughly classified into a thick film method comprising forming a semiconducting oxide material into particles, dispersing the particles in an organic vehicle to form a past, patterning the paste by screen printing or the like, and firing it, and a thin film method comprising depositing the semiconducting oxide film directly on a substrate in a vacuum, for example, by sputtering.

The thick film method is simple and, therefore, is low cost as compared with the thin film method, however, the sintering temperature must be elevated close to the melting point of the semiconducting oxide or a glass frit must be mixed so as to bind the semiconductor particles.

Furthermore, in the thick film method, the finished sensing film is a sintered body of large particles of a few μm or more and has a grain boundary and the thickness thereof is as large as, for example, about tens of μm. This is advantageous in that the surface area of the film is large and the reactivity of a gas detected within the film is improved, namely, the sensor sensitivity is enhanced, however, a problem is incurred that the response speed as a gas sensor is poor.

On the other hand, in the thin film method, a relatively thin and uniform bulk film having a thickness, for example, from sub-micron order to a few micron can be obtained, however, the process proceeds in a vacuum and this is disadvantageous in view of cost. Furthermore, the thin film method has a problem such that in the case where the sensing film is heat-treated as needed, the peripheral material such as Al wiring is limited by the heat resistance.

In addition, although the sensing film formed by the thin film method is small in the thickness and exhibits excellent response speed as a gas sensor, this is a uniform film reduced in the grain boundary and therefore, is small in surface area for reaction with a gas to be detected and disadvantageously exhibits poor sensor sensitivity.

In light of these problems, an object of the present invention is to make it possible to simply and easily form a sensing film for gas sensors, having excellent sensor properties such as sensitivity and response speed.

SUMMARY OF THE INVENTION

In order to attain the above-described object, the present inventors considered that, when a sintered body is formed from particles smaller than those for conventional sensing films formed by the thick film method and, thereby, a sensing film having a smaller thickness while having a grain boundary is formed, sufficiently high sensitivity and responsibility may be ensured.

However, to obtain a sintered body of particles smaller than those for conventional sensing films formed by the thick film method, the raw material particles in the paste must be in the nano-meter order. If the particles so small, the surface energy of individual particles becomes excessively large to cause aggregation of particles in the paste and a uniform paste cannot be obtained.

Therefore, extensive investigations have been made to uniformly disperse nano-meter order particles in a paste without causing aggregation. The present invention has been experimentally found based on the results of these investigations.

[1] A method for producing a gas sensor, comprising:
a step of mixing nano-meter order particles comprising a metal or a metal oxide, a dispersant for preventing aggregation of the particles, and a scavenger for trapping the dispersant at the sintering, in a solvent to prepare a paste body,
a step of coating the paste body on a base material, and
a step of firing the coated paste body to form a sensing film on the base material.

[2] The method as described in [1] above, wherein the particle has an average particle size of 2 to 100 nm.

[3] The method as described in [1] above, wherein the particle has an average particle size of 2 to 30 nm.

[4] The method as described in [1] to [3] above, wherein the sensing film has a thickness of 1 μm or less.

[5] The method as described in [1] to [3] above, wherein the sensing film has a thickness of 0.7 μm or less.

[6] The method as described in [1] to [5] above, wherein the particle is Sn or an Sn oxide and the sensing film is an Sn oxide.

[7] The method as described in [1] to [6] above, wherein the dispersant is a compound having a group containing a nitrogen, oxygen or sulfur atom and capable of coordinative bonding by the lone electron pair of the atom.

[8] The method as described in [7] above, wherein the dispersant is an amine compound having one or more terminal amino group.

[9] The method as described in [8] above, wherein the dispersant is an alkylamine.

[10] The method as described in [7] to [9] above, wherein the scavenger is a compound which, when heated, becomes to have reactivity with the group containing a nitrogen, oxygen or sulfur atom of the dispersant.

[11] The method as described in [10] above, wherein the scavenger is an organic acid, an organic acid anhydride, or a derivative thereof.

[12] The method as described in [1] to [11] above, wherein the paste body contains the scavenger in an amount of 1 to 2 times the stoichiometric amount for the reaction with the dispersant.

[13] The method as described in [1] to [11] above, wherein the firing is performed at a temperature of 300 to 600° C.

More specifically, the invention of [1] above is characterized in that in a method of producing a sensing film (40) for gas sensors on a base material (10) by sintering particles comprising a metal or a metal oxide, nano-meter order particles, a dispersant for preventing aggregation of the particles, and a scavenger for trapping the dispersant at the sintering are mixed in a solvent to prepare a paste body and this paste body is coated on the base material and burned to form the sensing film.

According to this method, in the paste body prepared by mixing nano-meter order particles, a dispersant and a scavenger in a solvent, the aggregation of particles is prevented by the dispersant, and a paste body where particles are uniformly dispersed in a solvent is obtained. The "paste body" as used herein includes a viscous liquid and, needless to say, a paste.

When this paste body is coated on a base material and fired (heated), the dispersant is trapped by the scavenger and therefore, in the nano-meter order particles, sintering starts and at the same time, oxidation starts.

The obtained sensing film is a sintered body of very small particles as compared with conventional thick film methods and a small film thickness in the level of conventional thin film methods can be realized. Furthermore, according to this production method, a sensing film can be produced by a simple process such as coating and firing (heating) of a paste body as in conventional thick film methods.

Therefore, according to the present invention, a sensing film for gas sensors, having excellent sensor properties such as sensitivity and responsibility can be simply and easily formed.

As in the invention of [6] above, the particles may be Sn or an Sn oxide and the sensing film (40) may be composed of an Sn oxide.

As in the invention of [7] above, the dispersant may be a compound having a group containing a nitrogen, oxygen or sulfur atom and capable of coordinative bonding by the lone electron pair of the atom. More specifically, an amine compound having one or more terminal amino group, represented by an alkylamine and the like, may be used.

As in the invention of [10] above, the scavenger may be a compound which, when heated, becomes to have reactivity with the group containing a nitrogen, oxygen or sulfur atom of the dispersant of [7] above.

As in the invention [13] above, the temperature at the time of firing the paste body coated on the base material (10) may be from 300 to 600° C.

This firing temperature is much lower than the firing temperature in conventional thick film methods using micron order particles, namely, the firing temperature close to the melting point of a semiconducting oxide, and can be attained due to use of nano-meter order particles. Therefore, peripheral materials of the gas sensor, such as Al wiring, are not limited by heat resistance.

The numerical reference in the parenthesis for denoting each means above is one example showing the corresponding relationship to the specific means in the embodiment described later.

BRIEF DESCRIPTION OF DRAWINGS

FIG. 1 is a schematic cross-sectional view of a gas sensor according to the embodiment of the present invention.

FIG. 3 is a view showing the results of X-ray diffraction analysis of a sensing film comprising tin oxide in the embodiment above.

MODES FOR CARRYING OUT THE INVENTION

Figure 2A:
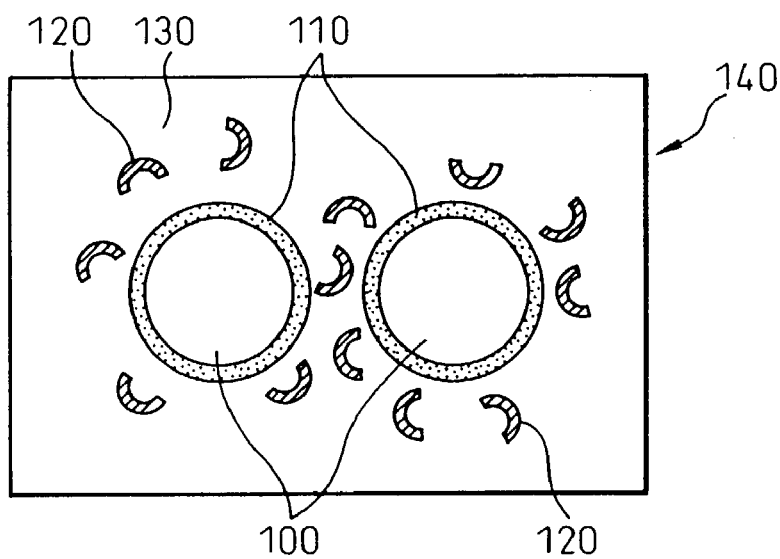
FIGS. 2A to 2C are each an explanatory view for explaining the production method of a sensing film in the embodiment above.

The present invention is described below by referring to the embodiment shown in the drawings. FIG. 1 is a view showing a schematic cross-sectional structure of a gas sensor S1 according to the embodiment of the present invention. This gas sensor S1 is used, for example, as a gas sensor for detecting a gas such as CO, $CH_4$, NO and $NO_2$.

In the gas sensor S1, a silicon oxide film 20 as an insulating film is formed on the entire surface of a silicon substrate 10 as the base material and a pair of detection electrodes 30 comprising a metal such as Al or an Al alloy, or a polycrystalline silicon (poly-Si) are formed on the silicon oxide film 20.

Furthermore, on the silicon oxide film 20, a gas sensing film 40 as a sensing film produced by the sintering of particles comprising a metal or a metal oxide is formed to cover the paired detection electrodes 30. In this example, the gas sensing film 40 is composed of a sintered body of Sn oxide ($SnO_x$) particles.

In the silicon substrate 10 positioned below the gas sensing film 40, a heater 50 as a diffused resistor is provided, for example, by forming a p-layer or n-layer region in the silicone substrate 10. This heater 50 can generate heat on passing a current and heat the gas sensing film 40.

For example, the gas sensor S1 can be operated as follows. A current is passed to the heater 50 and heat is thereby generated from the heater 50, as a result, the gas sensing film 40 is heated to a temperature where good sensitivity can be ensured.

The resistance value of the gas sensing film 40 changes according to the concentration of gas such as CO, $CH_4$, NO and $NO_2$ in the measuring environment and this change in the resistance value of the gas sensing film 40 is detected by detection electrodes 30, processed into signals by an external circuit or the like (not shown) and then output, whereby the gas can be detected.

Figure 2B:
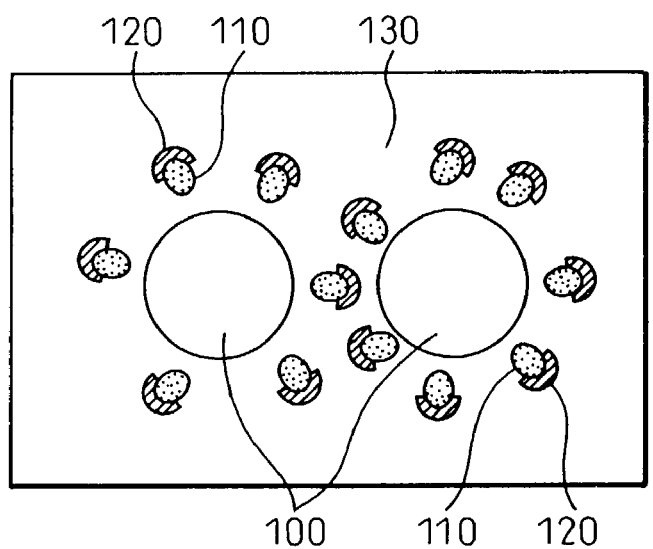
Figure 2C:
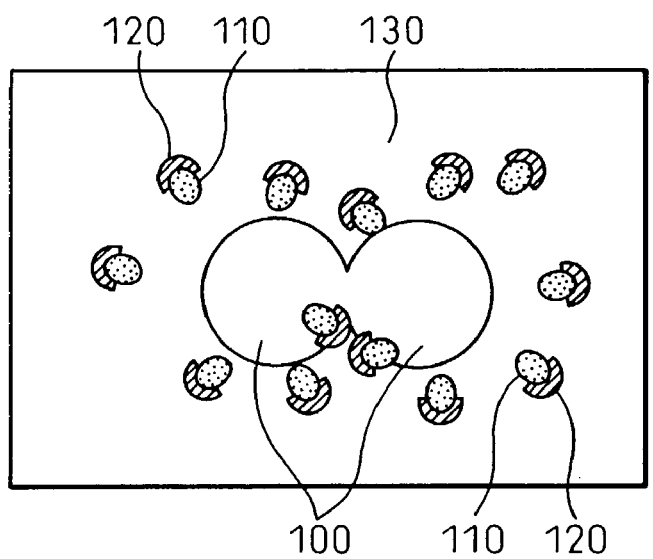

The production method of a gas sensing film 40 as the sensing film of the gas sensor S1 in this embodiment is described below by referring to FIGS. 2A to 2C. FIGS. 2A to 2C are each an explanatory view for explaining the production method.

As shown in FIG. 2A, nano-meter order particles 100, a dispersant 110 for preventing aggregation of the particles 100 and a scavenger 120 for trapping the dispersant 110 at the sintering are mixed in a solvent 130 to prepare a viscous liquid 140, namely, a paste body as a raw material of the sensing film. More specifically, particles 100 of which the surfaces are wet-treated with a dispersant 110 are mixed together with a scavenger 120 in a solvent 130.

The viscous liquid 140 is in the state where the surfaces of the nano-meter order particles 100 are covered with the dispersant 110, and the particles 100 covered with the dispersant 110 and the scavenger 120 are uniformly dispersed in the solvent 130.

In this state, the particles 100 formed as fine particles and thereby increased in the surface energy are prevented by the dispersant 110 from aggregating and therefore, the viscous liquid 140 is obtained as a paste body where the particles 100 are independently dispersed in the solvent 130.

The nano-meter order particles 100 are metal fine particles comprising a metal element which exhibits semiconducting property when oxidized, or a metal oxide fine particles having semiconducting property, and the particles are produced by an evaporation-in-gas method and has a diameter on the order from a few nm to tens of nm (from 2 to 100 nm, preferably from 2 to 50 nm, more preferably from 2 nm to 10 nm). In this example, the particles are Sn particles having a diameter of about 10 nm. The metal oxide fine particles can be produced by doping oxygen using an evaporation-in-gas method.

The compound used as the dispersant 110 makes a coordinative bond with the metal element constituting the particles 100 by utilizing a group having a lone electron pair on a nitrogen, an oxygen or a sulfur atom. Examples of the group containing a nitrogen atom include an amino group, examples of the group containing a sulfur atom include a sulfanyl group (—SH) and a sulfide-type sulfandiyl (—S—), and examples of the group containing an oxygen atom include a hydroxy group and an ether-type oxy group (—O—).

A representative example of the compound having an amino group, which can be used as the dispersant 110, is an alkylamine. The alkylamine in the state of forming a coordinative bond with the metal element is preferably not desorbed in a normal storage environment, more specifically, in the range not reaching 40° C. and preferably has a boiling point of 60° C. or more, more preferably 100° C. or more.

However, in the case of heat-treating (for example, heat-curing) the paste (viscous liquid 140), the alkylamine must be swiftly desorbable from the surface of the particles 100 and therefore, preferably has a boiling point at least not exceeding 300° C., usually in the range of 250° C. or less.

The alkylamine is, for example, an alkylamine where an alkyl group with C4 to C20, preferably from C8 to C18, is used and an amino group is present at the terminal of the alkyl chain. For example, the alkylamine with C8 to C18 is preferred in view of handleability, because this is thermally stable, the vapor pressure is not so high, and in the storing at room temperature or the like, the content can be easily maintained/controlled to fall in a desired range.

From the standpoint of forming the coordinative bonding, a primary amine-type compound generally exhibits higher bonding ability and is preferred. However, a secondary amine-type compound and a tertiary amine-type compound can also be used. Furthermore, a compound where two or more adjacent amino groups participate in the bonding, such as 1,2-diamine type and 1,3-diamine type, can also be used. In addition, a polyoxyalkyleneamine may also be used.

Other than these compounds having an amino group, which can be used as the dispersant 110, a hydroxyamine having a hydrophilic terminal group, for example, a hydroxyl group, in addition to the terminal amino group may also be used and examples thereof include ethanolamine.

A representative example of the compound having a sulfanyl group (—SH—), which can be used as the dispersant 110, is an alkanethiol. The alkanethiol in the state of forming a coordinative bond with the metal element is also preferably not desorbed in a normal storage environment and, more specifically, in the range not reaching 40° C. and preferably has a boiling point of 60° C. or more, more preferably 100° C. or more.

However, in the case of heat-treating (for example, heat-curing) the paste (viscous liquid 140), the alkanethiol must be also swiftly desorbable from the surface of the particle 100 and therefore, preferably has a boiling point at least not exceeding 300° C., usually in the range of 250° C. or less.

The alkanethiol is, for example, an alkanethiol where an alkyl group with C4 to C20, preferably from C8 to C18, is used and a sulfanyl group (—SH) is present at the terminal of the alkyl chain. For example, the alkanethiol with C8 to C18 is preferred in view of handleability, because this is thermally stable, the vapor pressure is not so high, and in the storing at room temperature or the like, the content can be easily maintained/controlled to fall in a desired range.

A primary thiol-type compound generally exhibits higher bonding ability and is preferred, however, a secondary thiol-type compound and a tertiary thiol-type compound can also be used. Furthermore, a compound where two or more sulfanyl groups (—SH) participate in the bonding, such as 1,2-dithiol type, can also be used.

A representative example of the compound having a hydroxy group, which can be used as the dispersant 110, is an alkanediol. Examples thereof include glycols such as ethylene glycol, diethylene glycol and polyethylene glycol.

The alkanediol in the state of forming a coordinative bonding with the metal element is also preferably not desorbed in a normal storage environment, more specifically, in the range not reaching 40° C. and preferably has a boiling point of 60° C. or more, more preferably 100° C. or more.

However, in the case of heat-treating (for example, heat-curing) the paste (viscous liquid 140), the alkanediol must be swiftly desorbable from the surface of the particle 100 and therefore, preferably has a boiling point at least not exceeding 300° C., usually in the range of 250° C. or less. For example, a compound where two or more hydroxy groups participate in the bonding, such as 1,2-diol type, can be more preferably used.

As such, the dispersant 110 is composed of a compound having a group containing a nitrogen, oxygen or sulfur atom, as the group capable of coordinative bonding with the metal element on the surface of the particles 100, and the dispersant covers the surface of the particles 100.

The scavenger 120 may be a compound which, when heated, becomes to have reactivity with the group containing a nitrogen, oxygen or sulfur atom of the dispersant 110 and examples thereof include an organic acid anhydride or a derivative thereof, and an organic acid.

The scavenger 120 is used for removing, on heating, the covering layer formed of the dispersant 110 which is a compound having a group containing a nitrogen, oxygen or sulfur atom.

More specifically, accompanying the heating, the scavenger reacts with the group containing a nitrogen, oxygen or sulfur atom of the dispersant 110, which is forming the covering layer of the particles 100 in the vicinity of room temperature. After this reaction, the group containing a nitrogen, oxygen or sulfur atom can hardly form a coordinative bonding with the metal atom on the surface of the particles 100 and, as a result, the covering layer is removed.

This removal function is not brought out in the vicinity of room temperature at which the paste is prepared and stored, and is exerted for the first time in the process of applying a heat treatment (sintering). More specifically, accompanying the heating, the acid anhydride or acid anhydride derivative added reacts with the dispersant 110 which is a compound having a group containing a nitrogen, oxygen or sulfur atom, such as a amine compound, thiol compound or diol compound, to form an amide, a thioester or an ester.

When this amide, thioester or ester is formed, the amine compound, thiol compound or diol compound covering the surface of the particle can hardly form a coordinative bonding with the metal atom any more, as a result, the covering layer by the dispersant 110 is removed.

By virtue of this action, the very fine particles 100 which are originally dispersed uniformly in the paste (viscous liquid 140) can provide a densely filled state. Before the heat treatment, the surface of the particle 100 is covered a layer composed of the dispersant 110 and therefore, the surfaces of particles 100 are prevented from directly contacting with each other, however, when the heat treatment proceeds and the covering layer is removed, the surfaces of particles 100 are put in a directly contacted state and the particles 100 undergo sintering with each other at a relatively low temperature.

Accordingly, the scavenger 120 which is an acid anhydride or an acid anhydride derivative and, in the process of removing the covering layer, is used for the reaction with the dispersant 110 of a compound having a group containing a nitrogen, oxygen or sulfur atom, is preferably added at least in excess of an amount equivalent to the total of the terminal amino group, sulfanyl group (—SH) and/or hydroxy groups contained in the amine compound, thiol compound and/or diol compounds.

The organic acid anhydride, a derivative thereof or the organic acid for use as the scavenger 120 is not particularly limited as long as it exhibits the above-described reactivity.

Examples of the organic acid which can be used include linear saturated carboxylic acids with C1 to C10, such as formic acid, acetic acid, propionic acid, butanoic acid, hexanoic acid, octylic acid, stearic acid, isostearic acid, oleic acid and linoleic acid; linear or branched saturated carboxylic acids with C1 to C18, such as acrylic acid, methacrylic acid, crotonic acid, cinnamic acid, benzoic acid and sorbic acid; various unsaturated carboxylic acids; various carboxylic acids such as dimeric acids and trimeric acids which are a polymerization product of an oleic acid, linoleic acid or the like, and dibasic acids (e.g., oxalic acid, malonic acid, sebacic acid, maleic acid, fumaric acid, itaconic acid, alkylsuccinic acid, alkenylsuccinic acid); and other organic acids having a phosphoric acid group (—O—P(O)(OH)$_2$) or a sulfo group (—SO$_3$H) in place of the carboxy group, such as phosphoric acid ester and sulfonic acid.

Examples of the organic acid anhydride or acid anhydride derivative which can be suitably used include aromatic acid anhydrides such as phthalic anhydride, trimellitic anhydride, pyromellitic anhydride, benzophenonetetracarboxylic anhydride, ethylene glycol bis(anhydrotrimellitate) and glycerol tris(anhydrotrimellitate); cyclic aliphatic acid anhydrides such as maleic anhydride, succinic anhydride, tetrahydrophthalic anhydride, methyltetrahydrophthalic anhydride, methylnadic anhydride, alkylsuccinic anhydride, alkenylsuccinic anhydride, hexahydrophthalic anhydride, methylhexahydrophthalic anhydride and methylcyclohexenetetracarboxylic anhydride; and aliphatic acid anhydrides such as polyadipic anhydride, polyazelaic anhydride and polysebacic anhydride.

Among these, methyltetrahydrophthalic anhydride, methylhexahydrophthlic anhydride, alkenylsuccinic anhydride and derivatives thereof are preferred, because these exhibit appropriate reactivity, for example, with the terminal amino group of the amine compound even at a relatively low heat-treatment (sintering) temperature.

The organic acid anhydride or acid anhydride derivative is used to react, at the heat-curing, with the dispersant 110 covering the surface of the particles 100, for example, an amine compound having a terminal amino group, such as alkylamine and polyoxyalkylamine, to form an amide.

Accordingly, the content of the acid anhydride or acid anhydride derivative as the scavenger 120 is appropriately selected according to the kind and content of the dispersant 110 which is a compound having a group containing a nitrogen, oxygen or sulfur atom and contained in the paste (viscous liquid 140), for example, alkylamine or polyoxyalkyleneamine used as the amine compound having a terminal amino group. In general, the scavenger is preferably used in an amount of at least 1 times, more preferably from 1 to 2 times, the stoichiometric amount for the reaction with the dispersant.

More specifically, for example, in the case of using an acid anhydride or acid anhydride derivative derived from a dibasic acid, such as methyl tetrahydrophthalic anhydride, methylhexahydrophthalic anhydride, alkenylsuccinic anhydride or a derivative thereof, the content (molar number) thereof is preferably an amount in excess of ½ of the sum total (molar number) of amine group derived from the amine compound having a terminal amino group, such as alkylamine or polyoxyalkyleneamine.

However, the content of the acid anhydride or acid anhydride derivative derived from the dibasic acid is preferably in the range of not exceeding 1 times the sum total (molar number) of the amine compound having a terminal amino group, such as alkylamine or polyoxyalkylamine.

In the case of using the organic acid but not the organic acid anhydride or a derivative thereof, the amount of the organic acid added is preferably selected from the above-described range assuming that two carboxyl groups, phosphoric acid groups (—O—P(O)(OH)$_2$) or sulfo groups (—SO$_3$H) correspond to one molecule of the acid anhydride derived from the dibasic acid.

The solvent 130 is not particularly limited, however, the solvent is preferably a non-polar or low polar solvent, not a solvent having high polarity such that the solubility of the dispersant 110 forming the covering layer on the surface of the particle 100, for example, an amine compound such as alkylamine, is excessively high and the covering layer disappears.

In addition, the solvent preferably has thermal stability to such an extent of not causing thermal decomposition even at a temperature where the heat-treatment (sintering) is preformed. In view of handleability, a non-polar or low polar solvent having a relatively high boiling point is preferred. For example, terpineol, mineral spirit, xylene, toluene, tetradecane and dodecane are suitably used.

A silicone substrate 10 is prepared as the base material where a heater 50, a silicon oxide film 20 and detection electrodes 30 are formed. In a predetermined region on one surface of the silicon substrate 10, the viscous liquid 140 is coated by screen printing or the like. Thereafter, the film of the coated viscous liquid 140 is fired at, for example, 300 to 600° C. to form a sintered body.

In this sintering process, as shown in FIG. 2B, the dispersant 110 is trapped by the scavenger 120, as a result, the dispersant 110 is removed from the surface of the nano-meter order particles 100 and the surface of the particles 100 is exposed. Then, as shown in FIG. 2C, the surfaces of particles 100 are put into contact with each other and sintering starts.

In the case of nano-meter order metal particles 100 like the Sn particles 100 of this example, the particle surface is exposed and the oxidation of the particles 100 starts. In other words, the metal particles 100 are oxidized and sintered.

After the completion of sintering, a gas sensing film 40 composed of a sintered body of semiconducting metal oxide fine particles is produced. In this example, a gas sensing film 40 composed of a sintered body of tin oxide (SnO$_x$) is produced.

The gas sensing film 40 finished by the production method in this embodiment is a sintered body of very small particles as compared with those in conventional thick film methods and not only has a grain boundary but also realizes a small film thickness (for example, on the order from sub-micron to a few microns) in the level of conventional thin film methods. Furthermore, according to the production method of the present invention, a gas sensing film 40 can be produced by a simple process such as coating and firing of a paste body 140 as in conventional thick film methods.

Therefore, according to this embodiment, a method for producing a sensing film, which can simply and easily form a sensing film for gas sensors having excellent sensor properties such as sensitivity and responsibility, can be provided.

In the production method of this embodiment, the particles 100 are ultrafine particles in the nano-order and therefore, the melting point lowers as compared with micron-order particles used for conventional thick film methods. This is based on the following generally known equation:

$$\Delta T/Tb = 2\gamma/(\rho \cdot Lb \cdot r)$$

wherein $\Delta T$ is a decrement of the melting point of particles, Tb is a melting point of bulk, $\gamma$ is a surface tension at solid-liquid interface, Lb is a heat of fusion of bulk and r is a radius of particle.

In other words, as the radius of particle becomes smaller, $\Delta T$ increases and the necessary firing temperature lowers, that is, sintering can proceed at a lower temperature. Furthermore, the particle surface becomes more active and the oxidation reaction also takes place at a lower temperature. More specifically, the firing temperature can be approximately from about 300 to 600° C. as described above.

FIG. 3 shows the results of x-ray diffraction analysis of the gas sensing film 40 in the example where a semiconducting tin oxide film as the gas sensing film 40 is formed using metal Sn ultrafine particles as the particles 100.

In FIG. 3, results when the firing temperature, namely, the sintering temperature is 300° C., 400° C., 500° C. or 600° C., and for comparison, results in the unfired case where the viscous liquid 140 prepared above is coated but not fired, are shown.

It is seen from FIG. 3 that peaks (in the Figure, peaks with a black triangular mark) of Sn appear in the unfired case whereas, when fired at a firing temperature of 300 to 600° C., peaks (in the Figure, peaks with a black circular mark) of tin oxide ($SnO_x$) appear, revealing that a semiconducting tin oxide film as the gas sensing film is formed.

The gas sensing film 40 produced by the production method of this embodiment is ensured with good sensor properties such as sensitivity and responsibility and this is verified below by referring to one specific example.

On a silicon substrate 10 where wiring such as detection electrodes 30 and a heater 50 were previously formed, a viscous liquid 140 having individually dispersed therein metal Sn particles 100 in a size of about 10 nm was coated in the region for the formation of a sensing film, namely, in the sensing part.

The dispersant 110 in the viscous liquid 140 used in this specific example was an alkylamine, the scavenger 120 was an organic acid anhydride, a derivative thereof or an organic acid, and the concentration of the particles 100 was 5%.

For the coating, various methods may be selected but as a simple and easy method, a method of dropping the liquid at a fixed rate using a microsyringe or the like, or a method of dipping the sensing part while masking other regions may be used. Furthermore, when the viscosity is appropriately adjusted, a coating method by ink jetting or screen printing may also be used.

The viscous liquid 140 coated as such was then fired by heat-treating it in an air at 400° C. to obtain a gas sensing film 40 of this example, which was a sintered film of tin oxide. The firing may be performed by using a normal belt furnace or batch furnace but in this example, a heat treatment was performed in a belt furnace for about 1 hour.

In this way, the above-described gas sensor S1 was formed, where a gas sensing film 40 (thickness: about 0.5 μm) composed of a tin oxide sintered body was formed on one surface of a silicon substrate 10. The gas sensing film 40 was formed to have a thickness of about 0.5 μm or about 1 μm and the former was designated as Specific Example 1 of this embodiment and the latter was designated as Specific Example 2 of this embodiment. The sensors S1 of Specific Examples each was installed in a sensor housing and then evaluated on the sensor properties.

The gases detected here were CO and $NO_2$ and each gas was introduced in a concentration of 100 ppm. After a predetermined time, the gases were changed over to fresh air and the output was examined. The output was examined by setting the temperature of the heater 50 to 300° C.

Also, a gas sensor S1 of a Comparative Example was produced, where the gas sensing film 40 was a tin oxide film (thickness: about 0.5 μm) formed by sputtering which is a conventional thin film method, and evaluated on the sensor properties in the same manner.

The sensor properties examined were sensitivity and responsibility. The sensitivity was determined as a resistance value variation $\Delta\Omega$. The resistance value variation $\Delta\Omega$ is a resistance value variation between the initial value before gases detected were introduced and the resistance value when the change after the introduction of gases was saturated. As the resistance value variation $\Delta\Omega$ is larger, the sensor sensitivity is higher.

The response time was a rising time from the introduction of gases detected until the change in the resistance value after the introduction of gases was saturated, that is, a time period necessary for causing resistance change in the above-described resistance value variation $\Delta\Omega$ portion. As this response time is shorter, the responsibility is better.

Gas Sensors S1 of Specific Examples and a gas sensor of a Comparative Example were examined on the sensitivity and response time for each of CO and $NO_2$ and the results are shown in the Table below.

|  | Film Thickness | CO | | $NO_2$ | |
| --- | --- | --- | --- | --- | --- |
|  |  | Sensitivity | Response Speed | Sensitivity | Response Speed |
| Example 1 | about 0.5 μm | about −70% | 3 sec or less | double or more digit change of resistance | 3 sec or less |
| Example 2 | about 1 μm | about −65% | 3 sec or less | double or more digit change of resistance | 3 sec or less |
| Comparative Example | about 0.5 μm | about −20% | 3 sec or more | single digit change of resistance | 3 sec or more |

It can be seen from the Table above that in Specific Examples 1 and 2, the sensitivity is greatly improved as compared with Comparative Example and the response speed is equal to or higher than that of Comparative Example employing a thin film method which ensures a high-level response speed among conventional techniques.

As such, according to this embodiment, the sensor sensitivity can be greatly improved while maintaining the responsibility in a level equal to or higher than the sensing film formed by a conventional thin film method. In other words, the sensing film formed by a conventional thin film method is low in sensitivity despite excellent responsibility, however, according to this embodiment, a sensing film excellent in both responsibility and sensitivity can be realized.

Figure 4:
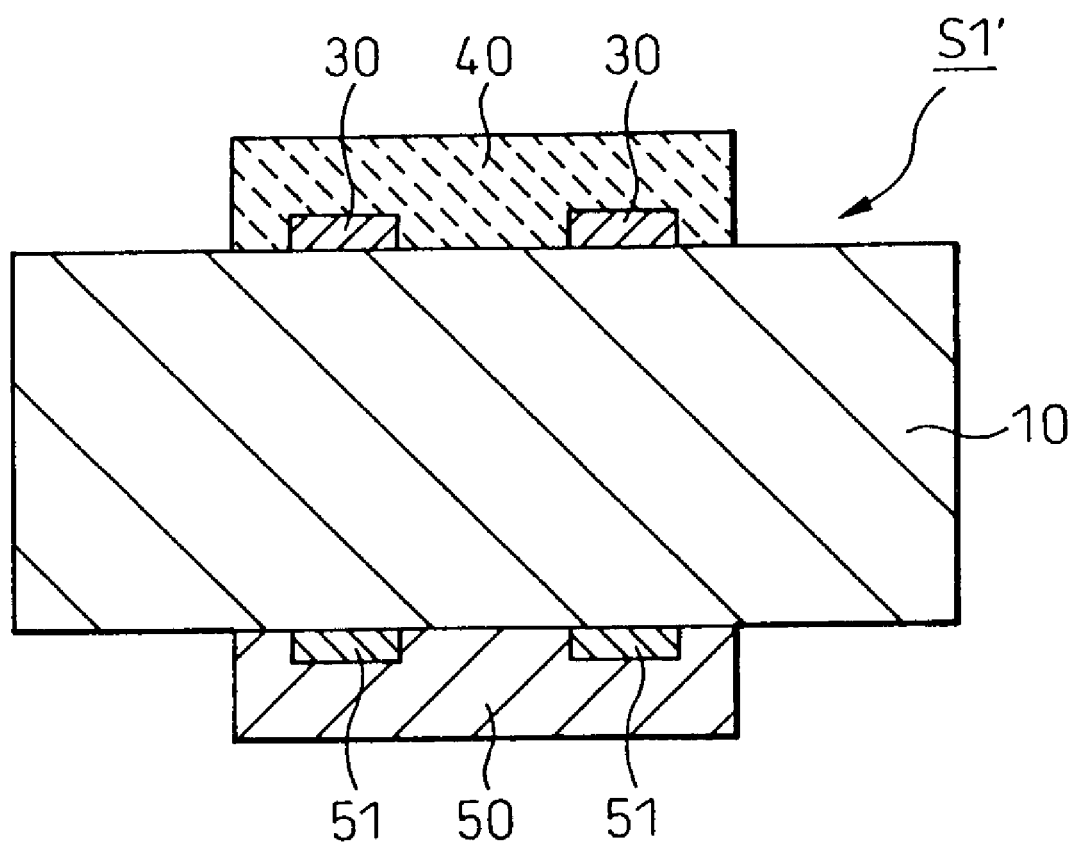
FIG. 4 is a schematic cross-sectional view of a gas sensor as a modified example of the embodiment above.

In a modified example of this embodiment, a ceramic substrate may be used for the substrate 10 as the base material. FIG. 4 shows a schematic cross-sectional structure of a gas sensor S1' as this modified example. In this case, a pair of detection electrodes 30 and a gas sensing film 40 are formed on one surface of the ceramic substrate 10 and in another surface side of the ceramic substrate 10 corresponding to the gas sensing film 40, a heater 50 having electrodes 51 for passing a current is formed as a resistance heating element.

As described in foregoing pages, the present invention is mainly characterized in that, in producing a sensing film 40 for gas sensors by sintering particles comprising a metal or a metal oxide on a base material 10, a paste body having dispersed therein a fine particulate raw material of nano-meter order, which has been conventionally unable to obtain, can be realized and a sensing film having excellent sensor properties can be easily and simply formed by using this paste body.

The invention claimed is:

1. A method for producing a gas sensor, comprising:
   a step of mixing nano-meter order particles comprising a metal or a metal oxide, a dispersant for preventing aggregation of said particles, and a scavenger which traps said dispersant at firing, in a solvent to prepare a paste body,
   a step of coating said paste body on a base material, and
   a step of firing said paste body coated to form a sensing film on the base material.

2. The method as claimed in claim 1, wherein said particles have an average particle size of 2 to 200 nm.

3. The method as claimed in claim 1, wherein said particles have an average particle size of 2 to 50 nm.

4. The method as claimed in claim 1, wherein said sensing film has a thickness of 1 µm or less.

5. The method as claimed in claim 1, wherein said sensing film has a thickness of 0.7 µm or less.

6. The method as claimed in claim 1, wherein said particle is Sn or an Sn oxide and said sensing film is an Sn oxide.

7. The method as claimed in claim 1, wherein said dispersant is a compound having a group containing a nitrogen, oxygen or sulfur atom and capable of coordinative bonding by a lone electron pair of said atom.

8. The method as claimed in claim 7, wherein said dispersant is an amine compound having one or more terminal amino group.

9. The method as claimed in claim 8, wherein said dispersant is an alkylamine.

10. The method as claimed in claim 7, wherein said scavenger is a compound which, when heated, becomes to have reactivity with the group containing a nitrogen, oxygen or sulfur atom of said dispersant.

11. The method as claimed in claim 10, wherein said scavenger is an organic acid, an organic acid anhyd ride, or a derivative thereof.

12. The method as claimed in claim 1, wherein said paste body contains said scavenger in an amount of 1 to 2 times the stoichiometric amount for the reaction with said dispersant.

13. The method as claimed in claim 1, wherein said firing is performed at a temperature of 300 to 600° C.

14. A method for producing a sensing film, the method comprising:
   providing nano-meter order particles;
   providing a dispersant for preventing aggregation of the nano-meter order particles;
   providing a scavenger for trapping the dispersant;
   preparing a paste body by mixing the nano-meter order particles, the dispersant and the scavenger in a solvent, the dispersant preventing aggregation of the nano-meter order particles in the paste body;
   coating the paste body on a base material;
   firing the paste body after coating the paste body on the base material to form the sensing film on the base material, the scavenger trapping the dispersant during the firing of the paste body.

* * * * *

UNITED STATES PATENT AND TRADEMARK OFFICE
CERTIFICATE OF CORRECTION

PATENT NO. : 7,070,829 B2
APPLICATION NO. : 10/386831
DATED : July 4, 2006
INVENTOR(S) : Masashi Totokawa et al.

It is certified that error appears in the above-identified patent and that said Letters Patent is hereby corrected as shown below:

Col. 11, line 46, claim 2, "200 nm" should be --100 nm--

Signed and Sealed this

Twenty-eighth Day of August, 2007

JON W. DUDAS
*Director of the United States Patent and Trademark Office*